United States Patent [19]

Miura et al.

[11] Patent Number: 4,821,576
[45] Date of Patent: Apr. 18, 1989

[54] AUTOMATIC CLEANING DEVICE FOR USE IN THE THERMOPLASTICS EXTRUSION PLASTOMETER

[75] Inventors: Yashuhiro Miura, Chiba; Hiromu Iwata, Kisarazu, both of Japan

[73] Assignee: Sumitomo Chemical Company, Limited, Osaka, Japan

[21] Appl. No.: 154,582

[22] Filed: Feb. 10, 1988

[30] Foreign Application Priority Data

| Feb. 10, 1987 | [JP] | Japan | 62-027360 |
| Feb. 10, 1987 | [JP] | Japan | 62-027361 |
| Feb. 10, 1987 | [JP] | Japan | 62-027362 |
| Feb. 10, 1987 | [JP] | Japan | 62-027363 |

[51] Int. Cl.$^4$ .................................... G01N 11/00
[52] U.S. Cl. .................................... 73/788; 15/4; 425/225
[58] Field of Search .................... 15/4; 425/225, 226, 425/227, 228; 73/788

[56] References Cited

U.S. PATENT DOCUMENTS 4,255,109  3/1981  Emmerich et al. .................. 425/227

FOREIGN PATENT DOCUMENTS

| 2140619 | 2/1973 | Fed. Rep. of Germany . |
| 3013797 | 11/1980 | Fed. Rep. of Germany . |
| 2302782 | 10/1976 | France . |
| 871039 | 12/1979 | U.S.S.R. . |
| 1507402 | 4/1978 | United Kingdom . |

*Primary Examiner*—Stewart J. Levy
*Assistant Examiner*—Michele Simons
*Attorney, Agent, or Firm*—Birch, Stewart, Kolasch & Birch

[57] ABSTRACT

In an automatic cleaning device for use in the thermoplastics extrusion plastometer including a piston cleaning unit, a conveying unit, a cylinder cleaning unit and a die cleaning unit. The piston cleaning unit cleans the surface of the piston at plasticity testing positions. The conveying unit moves the cylinder from the plasticity testing position to a cylinder cleaning position and to a die cleaning position. The cylinder cleaning unit cleans the interior surface of the cylinder at a cylinder cleaning position. Finally, the die cleaning unit cleans the interior surface of the die at the die cleaning position.

34 Claims, 13 Drawing Sheets

AUTOMATIC CLEANING DEVICE FOR USE IN THE THERMOPLASTICS EXTRUSION PLASTOMETER

BACKGROUND OF THE INVENTION

This invention relates to a thermoplastics extrusion plastometer cleaning device, especially, a device for cleaning automatically the cylinder, piston and die of the extrusion plastometer for testing the plasticity of the thermoplastics.

The extrusion plastometer tests the plasticity of the thermoplastics. The test is carried out by extruding melted thermoplastics through a die of a stipulated length and bore at a stipulated temperature and under stipulated pressure to measure the extrusion speed. There are two procedures for the test; Procedure A and Procedure B (stipulated by JIS). In procedure A, a mass which is extruded in a unit hour is manually cut off to be measured. In Procedure B, a time in which a unit of mass is extruded is measured. The plasticity of the melted polymer materials, such as thermoplastics, is related with the shearing speed thereof. The result of the plasticity test provides one index for their forming. Thus the plasticity test is important. This invention is usable in cleaning the cylinders, pistons and dies used in both of the above described Procedures A and B.

The procedures of the plasticity test on the thermoplastics are stipulated in detail in JISK7210 1976 and are not referred to herein. The portion of the procedures which is related with this invention and pertains to the manual measurement will be briefed.

The prior art manually operated test device has an electric furnace and a stipulated quantity of a test specimen is placed in a metal cylinder which has been controlled to have a measurement temperature by the electric furnace and melted. A weight of a stipulated mass is mounted on a piston inserted into the cylinder to extrude the melted specimen downward through a die of small bore arranged in the bottom part of the cylinder. When the test is completed in accordance with Procedure A or B, a manual force is applied to the weight to force the specimen residue in the cylinder down out of the cylinder through a die. Before a test is started anew, the part of the specimen for a last test sticking to the cylinder, piston and die has to be perfectly removed therefrom. Otherwise correct measurement cannot be made. Conventionally the cylinder has been cleaned by sliding a cylinder cleaning rod with soft cloth wound thereon. The cleaning was carried out by sliding the cylinder cleaning rod manually twice to three times in the cylinder.

And the piston cleaning has been carried out by wiping off the residual specimen on the piston surface with a soft cloth by an examiner.

Moreover, the die cleaning was carried out with a brass or wooden rod by taking out the die from the bottom of the cylinder after the cylinder cleaning.

The cleaning described above must be carried out essentially before a test. Without the cleaning undesirable specimen residue of a last test affects the following test. The cleaning has to be carried out at high temperatures since the cylinder is heated up to a high temperature as high as 125° to 300° C., which varies depending on specimens. Otherwise the specimen residue is cured, and it becomes difficult to remove it.

The conventional cleaning of the cylinder has been carried out manually since no suitable automatic cleaning means has been available. Such manual cleaning has been accompanied by the following disadvantages, safety problems due to the cleaning of the cylinder under a high temperature, increased costs due to the manual cleaning; lower precision of the measurement due to a nonuniform cleaning of the cylinder. Because of these disadvantages, an automatic cleaning of the cylinder has been earnestly expected.

SUMMARY OF THE INVENTION

The object of this invention is to provide a cylinder cleaning device for cleaning the cylinder of the extrusion plastometer of the thermoplastics, which enables the cylinder cleaning to be automated, whereby the safety is improved, labor is saved, and the precision of the measurement is improved.

This invention realizes the automation of the cleaning operation of the thermoplastics extrusion plastometer and comprises:

a piston cleaning unit for removing a piston from a cylinder to clean the surface of the piston at a plasticity testing position; a conveying unit for moving the cylinder from the plasticity testing position sequentially to a given cylinder cleaning position and to a die cleaning position; a cylinder cleaning unit for cleaning the interior surface of the cylinder Conveyed from the plasticity testing position to the cylinder cleaning position: and a die cleaning unit for cleaning the interior surface of the die conveyed from the cylinder cleaning position to the die cleaning position, without removing the die from the cylinder.

DETAILED DESCRIPTION OF THE INVENTION

Figure 1:
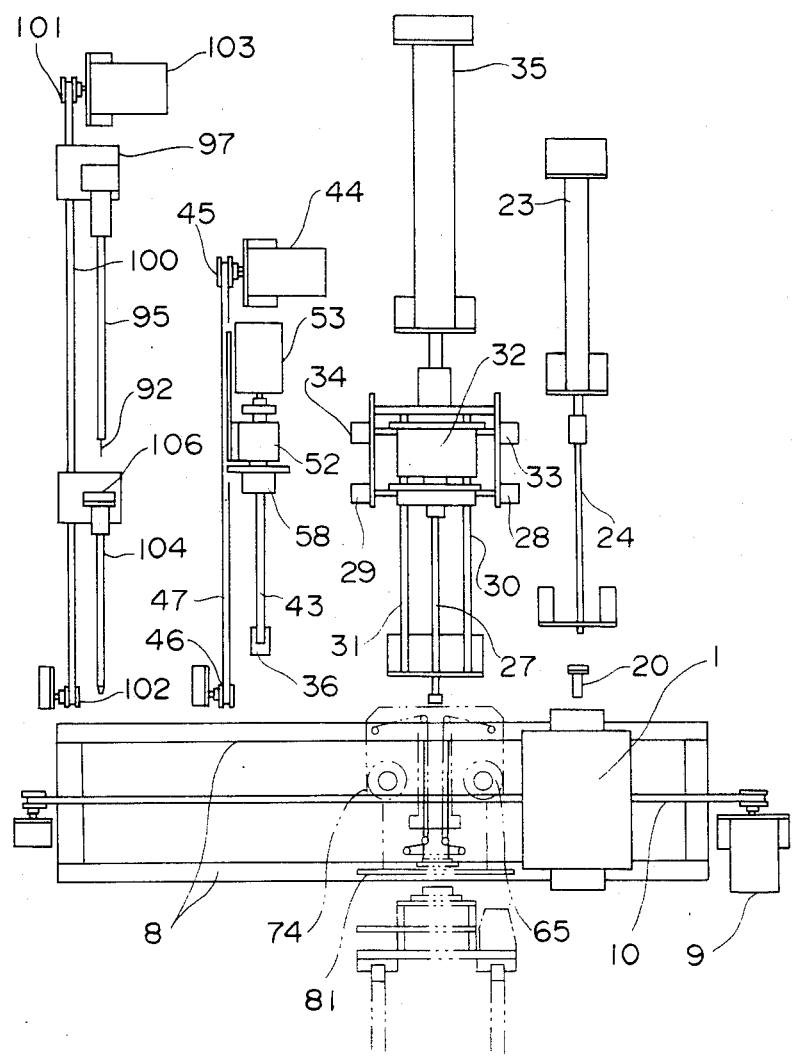
FIG. 1 is a front view of the general structure of the full automatic extrusion plastometer using the automatic cleaning device according to one embodiment of this invention.

As shown in FIG. 1, the plastometer comprises an electric furnace, a conveying unit, a test specimen charging unit, a piston unit, a piston cleaning unit, a cylinder cleaning unit, and a die cleaning unit. The electric furnace 1 incorporates a cylinder, a die, a heater, etc. The conveying unit contains a slide rail 8 arranged horizontally, a stepping motor 9 for moving the electric furnace, etc. The test specimen charging unit contains a guide pipe 20, a specimen extruding rod arranged vertically, etc. The piston unit contains a piston 27 driven up and down, a weight 32, etc. The piston cleaning unit contains bobbins 65 and 74, a piston cleaning mechanism 81, etc. and is disposed in front of a side of the slide rail 8 movable toward and away from the slide rail 8. The cylinder cleaning unit contains a pad 36, a cylinder cleaning mechanism 52 for driving the pad 36 vertically, etc. The die cleaning unit contains a die cleaning rod holder 95, a guide pipe 104, etc.

The electric furnace 1 is attached vertical to the slide rail 8 for moving the electric furnace 1. The stepping motor 9 and the timing belt 10 correctly moves the electric furnace 1 sequentially to a specimen charging position, a plasticity testing position (measuring position), a cylinder cleaning position and a die cleaning position. The piston cleaning unit is disposed on a different slide rail perpendicular to the side rail 8. When a plasticity measuring test is completed, the electric furnace 1 moved to the cylinder cleaning position along the slide rail 8, and the piston cleaning unit is advanced toward the slide rail 8.

Next, the structure and the operation of the specimen charging unit will be explained in detail with reference to FIGS. 2, 3 and 4.

Figure 2:
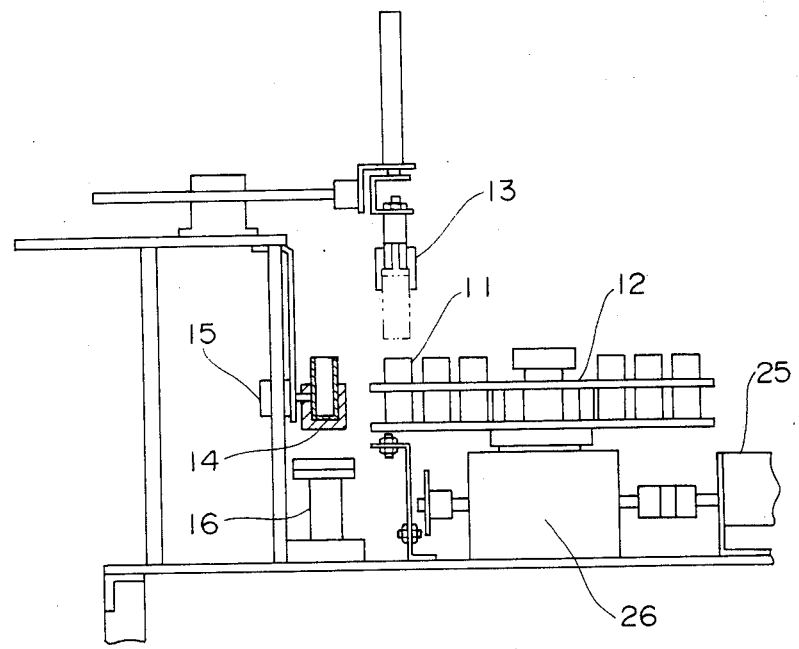
FIG. 2 is a side elevational view of the specimen bottle taking-out mechanism of the specimen charging unit.
Figure 3:
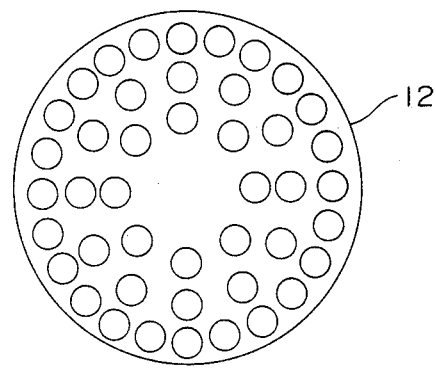
FIG. 3 is a plan view of the specimen table.

FIG. 2 shows a specimen bottle taking out mechanism for taking a specimen bottle 11 from a specimen table 12. FIG. 3 shows the specimen table 12 in FIG. 2. FIG. 4 shows a specimen charging mechanism for supplying to the cylinder in the electric furnace 1 the specimen in a specimen bottle 11 taken out by the mechanism of FIG. 2.

The specimen is charged in the following manner. The specimen is beforehand scaled in a stipulated amount, and the stipulated amount is put in a bottle 11. A required number of the bottles 11 for a test are arranged on the specimen table 12. When the bottles 11 are arranged on the specimen table 12 and the electric furnace 1 is heated, the extrusion plastometer using the automatic cleaning device of this invention will be actuated.

When the plastometer is actuated, as shown in FIG. 2, a specimen taking out robot 13 is actuated to take out one of the specimen bottles 11 from the specimen table 12 to convey the bottle 11 to the specimen holder 14. The specimen bottle 11 held by the specimen holder 14 is turned by 180° together with a rotary actuator 15, and the specimen in the bottle 11 is shifted into a linear vibrating feeder 16. The linear vibrating feeder 16 begins to feed the specimen. The specimen is fed into the cylinder 3 in the electric furnace 1 through a funnel 17, a specimen feed hose 18, a funnel 19, and the guide pipe 20. At this time, the guide pipe 20 is in close contact with the top of the electric furnace by an air cylinder 21.

All the specimen cannot be charged at once in view of the requirement to exhaust the air from the specimen. When a half of the specimen is fed, the linear vibrating feeder 16 is stopped and the funnel 19 is turned by 90° by the rotary actuator 22.

Figure 4:
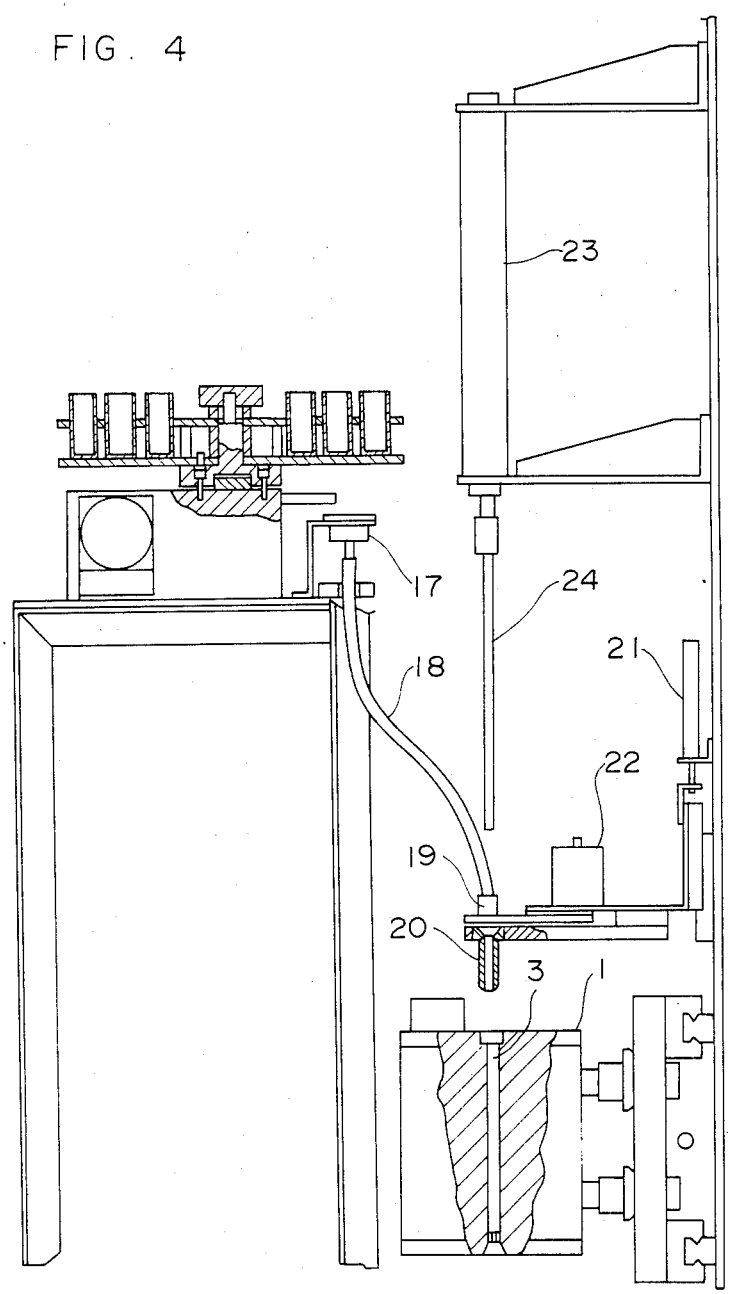
FIG. 4 is a side elevational view of the mechanism of the specimen charging unit for feeding the specimen taken out from the specimen table to the cylinder.

Then, an air cylinder 23 in FIG. 4 is actuated to move the specimen extruding rod 24 downward to push the specimen in the electric furnace 1 into the cylinder 3. When the specimen has been pushed into the cylinder 3, the specimen extruding rod 14 is lifted to its original position. When the specimen extruding rod 24 is lifted, the funnel 19 is returned to its original position by the rotary actuator 22 to receive the remaining half of the specimen. When the remaining half of the specimen reaches the electric furnace 1, the specimen extruding rod 24 is actuated to push the specimen into the cylinder 3 in the electric furnace When all the specimen has been charged, the guide pipe 20 in FIG. 4 is lifted by the air cylinder 21 to its original position. The specimen holder 14 in FIG. 2 is turned by 180° by the rotary actuator 15 to its original position to have the empty bottle 11 returned to its original position on the specimen table 12 by the robot 13.

Next, the structure and operation of the mechanism for measuring the plasticity will be explained in good detail. When the above described operation of feeding the specimen is completed, an index drive 26 is actuated by an induction motor 25 in FIG. 2. Accordingly the specimen table 12 is also turned, so that a next one of the specimen bottles 11 is moved to the specimen taking out position by the robot 13. Meanwhile the electric furnace 1 is moved from its specimen charging position to its measuring position (plasticity testing position by the stepping motor 9 for moving the electric furnace 1. Then, in the condition shown in FIG. 1 air cylinders 28 and 29 are unlocked, so that the piston 27 having an adjusted weight lowers itself by its own weight along guide rods 30 and 31 into the cylinder 3 in the electric furnace 1.

In this condition, the specimen is melted in the electric furnace 1 which is controlled to have a given temperature. The air bubbles in the cylinder 3 are expelled through the die by the piston 27 (the exhausting of air from of the specimen). Depending on the types of specimens, a weight 32 may be added to the piston 27, and air cylinders 33 and 34 are unlocked, so that the mass of the weight is added to the piston 27. This allows a larger load to push the specimen.

The measurement of the plasticity is given by measuring a time in which the lower end surface of the piston 27 lowers a stipulated distance from the top surface of the die 6 (Procedure B). For example, the displacement of the piston 27 is measured by using a non contact magnetic deformation sensor (not shown). The voltage signals from the sensor are inputted in a computer as the measurement start and finish signals so as to measure a time, and based on the time the MFR (melt flow rate) value is given by the following formula:

$$\text{MFR (T.M.B.)} = 426 \times L \times \rho/t$$

wherein
T: Measured temperature (°C.)
M: Test load (Kg f)
B: Procedure B
L: Displacement distance of the piston (cm)
$\rho$: Density of resin at the test temperature (g/cm 3)

t: Average (s) of the times in which the piston moves over a length L)

426: (The average of the areas (cm 2) of the piston and the cylinder)×600 seconds.

When a measurement is finished, an air cylinder 35 for discharging the specimen residue lowers the weight 32, and the weight 32 forces out the specimen residue. When the specimen residue has been discharged, the air cylinder 35 begins to go up. At this time, the air cylinders 28,29,33,34 are actuated to lock the piston 27 and the weight 32, and the whole is lifted by the air cylinder 35. When a measurement is finished, the electric furnace 1 is moved correctly to the cylinder cleaning unit by the stepping motor 9.

Next, the cylinder, piston and die cleaning which characterizes his invention will be explained in good detail.

First, the structure and the operation of the cylinder cleaning unit will be explained in good detail with reference to FIGS. 5, 6, 7, 8, 9 and 10.

Figure 5:
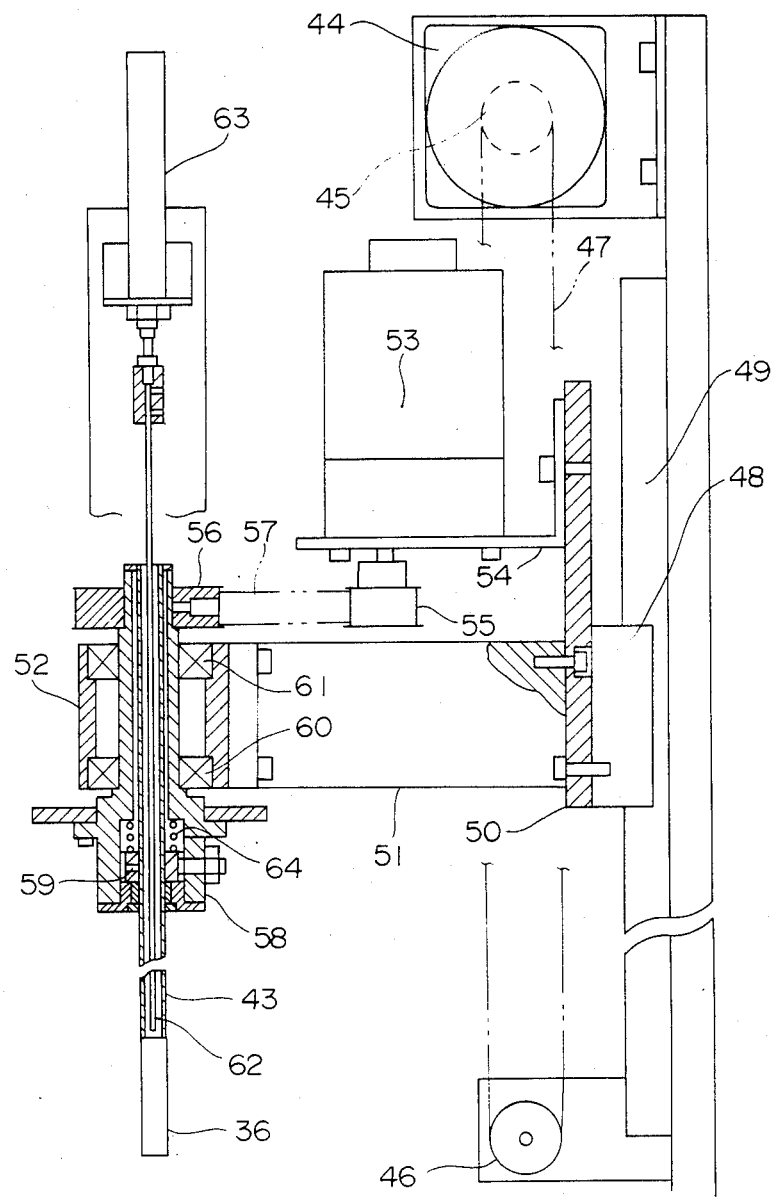
FIG. 5 is a side elevational view of the general structure, partly in cross section, of the cylinder cleaning unit.

FIG. 5 is a partially sectional side view of a cylinder cleaning unit. As shown in FIG. 5, a motor 44 is fixed to the top of a guide rail 49 erected. A pulley 45 is mounted on the rotary shaft of the motor 44. An idle pulley 46 is mounted on the lower end of the guide rail 49. A timing belt 47 is wound on the pulleys 45 and 46. This arrangement enables a bracket 51 attached to a guide 48 through an applicator 50 to move up and down in accordance with the rotations of the motor 44.

A cylinder cleaning mechanism 52 is fixed to the forward end of the bracket 51. A cleaning rod housing 58 is arranged vertically at the central portion of the mechanism 52. At the central portion of the housing 58 is disposed a cylindrical cylinder cleaning rod 43. A pad extruding rod 62 is arranged at the central portion of the cylinder cleaning rod 43 and is moved up and down by an air cylinder 63 disposed at an upper portion of the cylinder cleaning mechanism 52.

On the other hand, an L-shaped fixture 54 is fixed to the applicator 50. A motor 53 is fixed to the L-shaped fixture 54. A pulley 55 is mounted on the rotary shaft of the motor 53. The pulley 55 is interrelated through a timing belt 57 with a pulley 56 fixed to the housing 58. This arrangement enables the housing 58 and the cylinder cleaning rod 43 to be rotated by the motor 53.

Bearings 60 and 61 make the rotation of the housing 58 smooth. A spring 64 absorbs a shock which should act upwardly onto the cylinder cleaning rod 43. A pusher screw 59 secures the cylinder cleaning rod 43.

Next the structure of the forward portion of the cylinder cleaning rod 43 will be explained.

Figure 6:
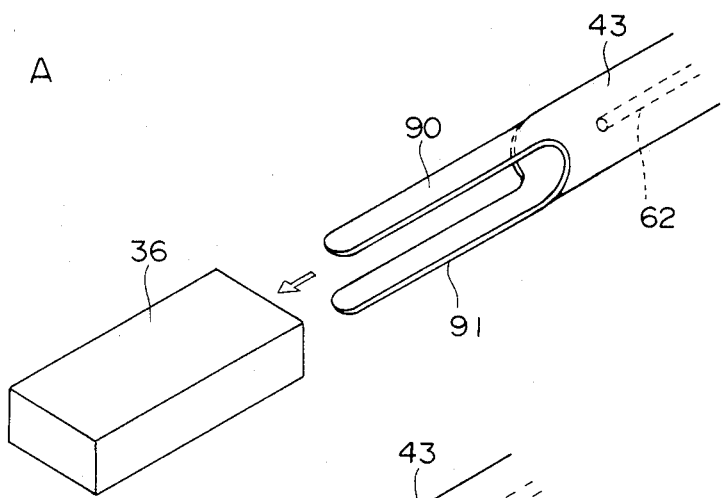
FIGS. 6A, 6B and 6C are perspective views explaining the structure and function of the cylinder cleaning rod.
Figure 6:
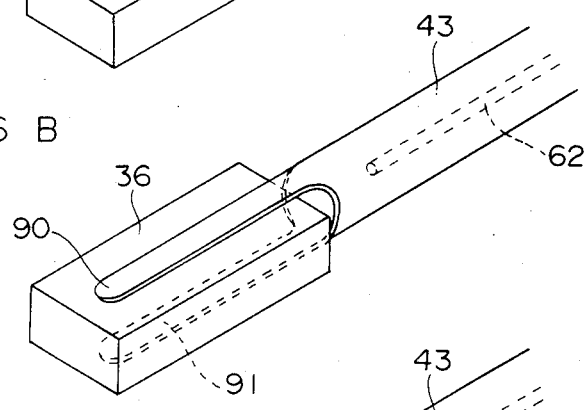
Figure 6:
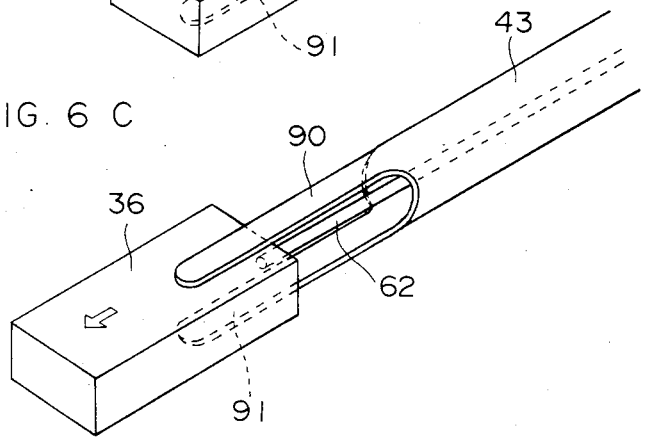

As shown in FIG. 6, the forward end of the cylinder cleaning rod 43 is bisected by projection spring members 90 and 91. The pad extruding rod 62 is disposed at the central portion of the cylinder cleaning rod 43. As shown in FIG. 6A, when the cylinder cleaning rod 43 is advanced toward a pad 36 in the direction indicated by the arrow in FIG. 6 A), the two spring members 90,91 hold he pad 36 therebetween as shown in FIG. 6B. Then in the condition as shown in FIG. 6B, when the pad extruding rod 62 is actuated, the pad 36 is pushed in the direction indicated by the arrow in FIG. 6C and released from the cylinder cleaning rod 43.

Then, a pad feed mechanism for supplying a pad to the cylinder cleaning rod 43 will be explained with reference to FIGS. 7 and 8.

Figure 7:
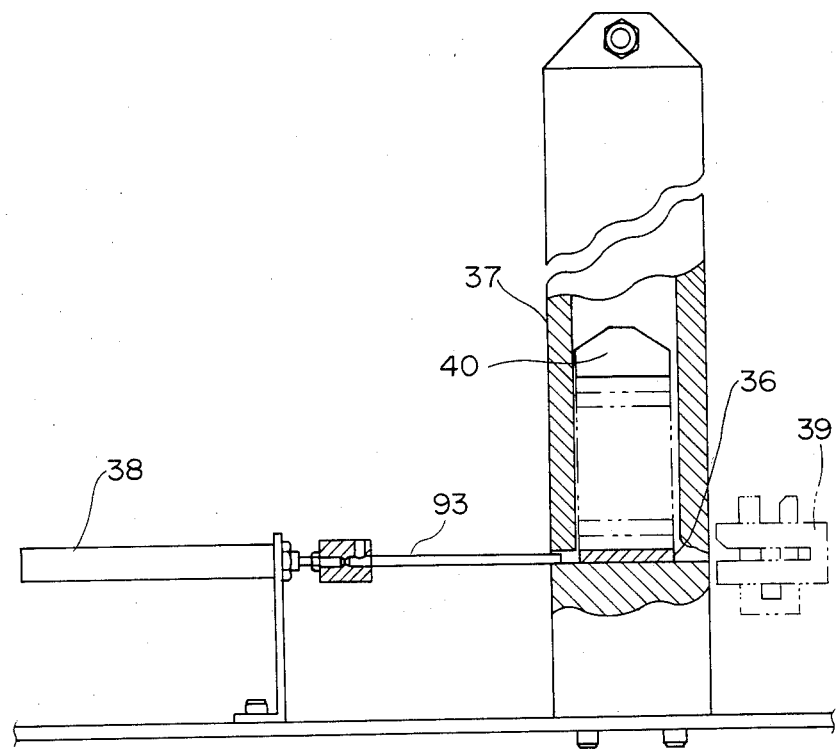
FIG. 7 is a side elevational view, partly in cross section, of a pad stocker and its surroundings.

As shown in FIG. 7, a plurality of pads 36 are stacked in the pad stocker 37 which is erected. The pad stocker 37 has an opening in the opening thereof, which is large enough for a pad pushing rod 93 to intrude therein and an opening in the surface opposite to the opening, which is large enough for a pad to be pushed out therefrom. The pad pushing rod 93 can be driven horizontally by an air cylinder for pushing a pad. A pad 36 pushed out from the pad stocker 37 can be received in a pad holder 39 illustrated by the two-dot chain line. A weight 40 moves a pad 36 downward.

Figure 8:
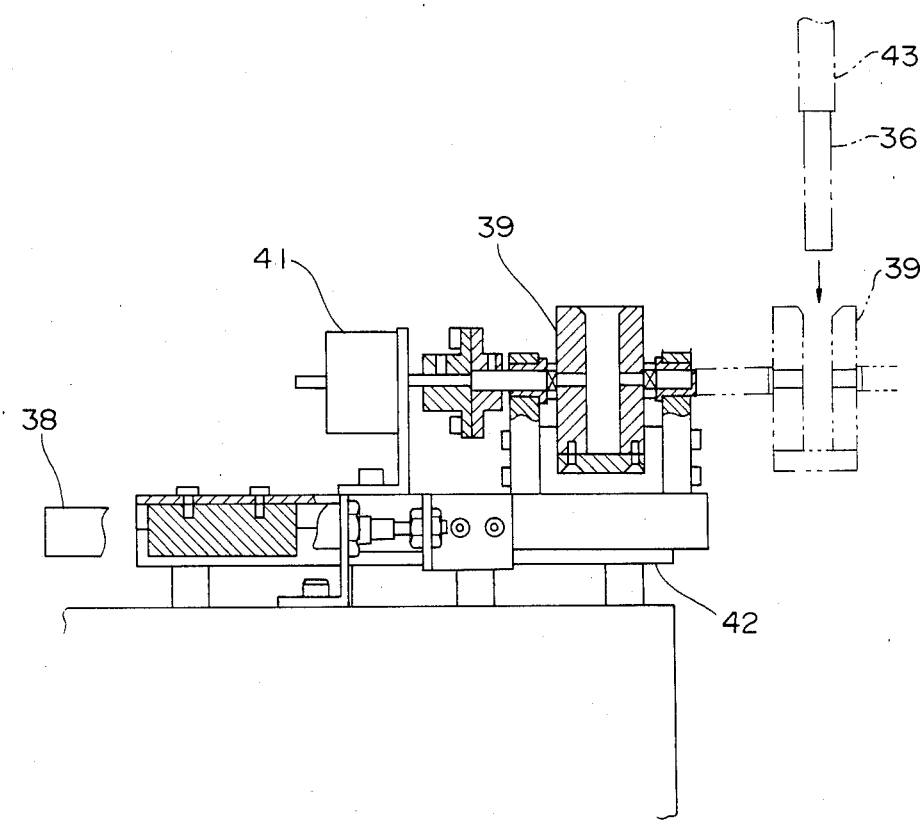
FIG. 8 is a side elevational view, partly in cross section, of a pad holder and its surroundings.

As shown in FIG. 8, the pad holder 39 can be rotated by 90° by a rotary actuator 41, and the whole device can be moved horizontally along a slide rail 42.

Next, the operation of the embodiment shown in FIGS. 5 through 8 will be sequentially explained.

When a plasticity test is completed, the electric furnace moves to a position where the cylinder is cleaned. That is, the cylinder in the electric furnace is located directly under the cylinder cleaning rod 43 shown in FIG. 5. Immediately thereafter, he air cylinder 38 for pushing a pad is actuated, and the pad pushing rod 93 pushes out an undermost one of the stacked pads in the pad stocker 37. The pad thus pushed out is held between the pad holders 39. Then the pad pushing rod 93 returns to it original position. The remaining pads 36 in the pad stocker 37 are lowered by the weight 40.

Then, the pad holder 39 holding the pad 36 is turned by 90° by the rotary actuator 41 in FIG. 8 into the condition shown in FIG. 8. Then the pad holder 39 moves to the right along the slide rail 42 until the position indicated by a two-dot chain line in FIG. 8. At this time the forward end of the cylinder cleaning rod 43 is directly above the pad holder 39 indicated by a two-dot chain line in FIG. 8. Then the cylinder cleaning rod 43 is lowered in the sequence shown in FIGS. 6A and 6B, and the spring members 90, 91 hold the pad 36. The cylinder cleaning rod 43 is lowered by the motor 44 in FIG. 5.

When the pad 36 has been held in the forward end of the cylinder cleaning rod 43, the pad holder 39 in the position shown in FIG. 8 returns to its original position. Then the cylinder cleaning rod 43 is driven further downward by the motor 44 to enter the cylinder within the electric furnace. At this time the pad 36 has been rotated by the motor 53 through the cylinder cleaning rod, the cylinder cleaning rod housing 58, the timing belt 57, etc. The pad 36 cleans the interior of the cylinder while rotating and moving up and down.

When the pad 36 finishes cleaning the interior of the cylinder, the cylinder cleaning rod 43 is driven by the motor 44 upward out of the cylinder. Then, the pad extruding rod 62 is driven downward by the air cylinder 63 in FIG. 5, and the pad 36 is released from the spring members 90, 91 as shown in FIG. 6C to drop onto a suitable tray or the like (not shown).

The embodiment described above in good detail dispenses with manual operation in cleaning the cylinder and completely automates the cleaning of the cylinder.

The cylinder cleaning unit is not limited to the above-described embodiment and includes reforms, modifications and variations without departing from the scope of the claims.

According to the above-described embodiment, all the steps of feeding a pad, cleaning the cylinder and releasing the pad are completely automated. But it is possible to make only the step of feeding a pad manual. That is, without using the members shown in FIGS. 7 and 8, a pad 36 may be manually attached to the forward end of the cylinder cleaning rod 43 in FIG. 5.

Figure 9:
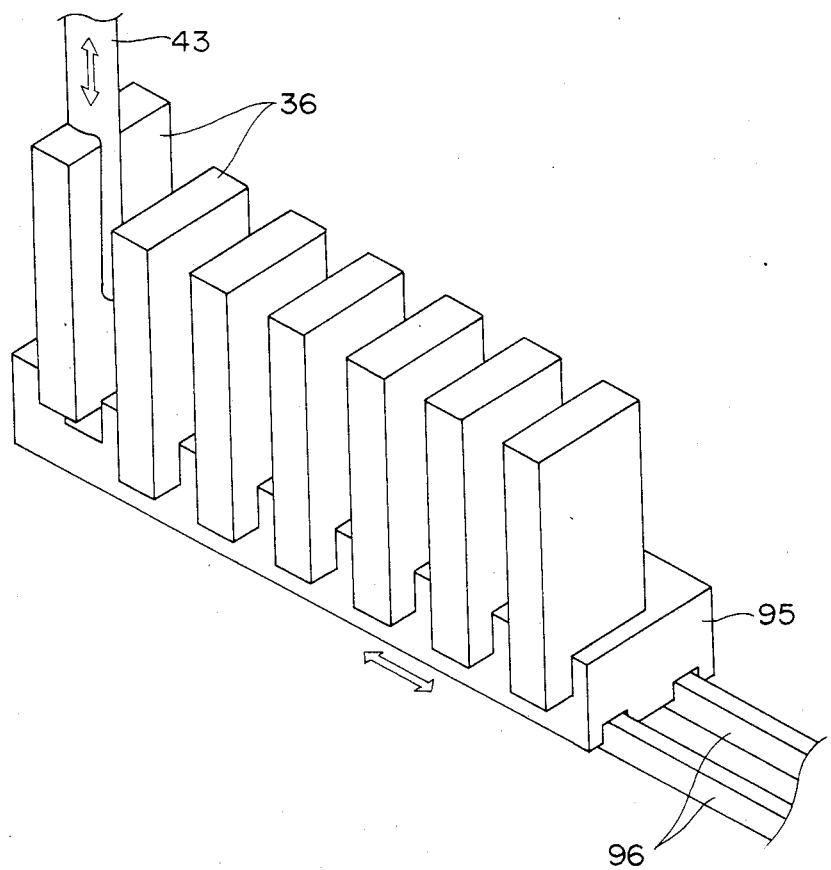
FIG. 9 is a perspective view of a main portion of a modification of the pad stocker.

In place of the members of FIGS. 7 and 8, the member as shown in FIG. 9 may be used. That is, a plurality of pads 36 are placed beforehand in a cassette 95, and the cassette 95 may be moved along the slide rail 96. In this case, it is necessary to control the displacement amount of the cassette 95 by a microcomputer or other control device.

Figure 10:
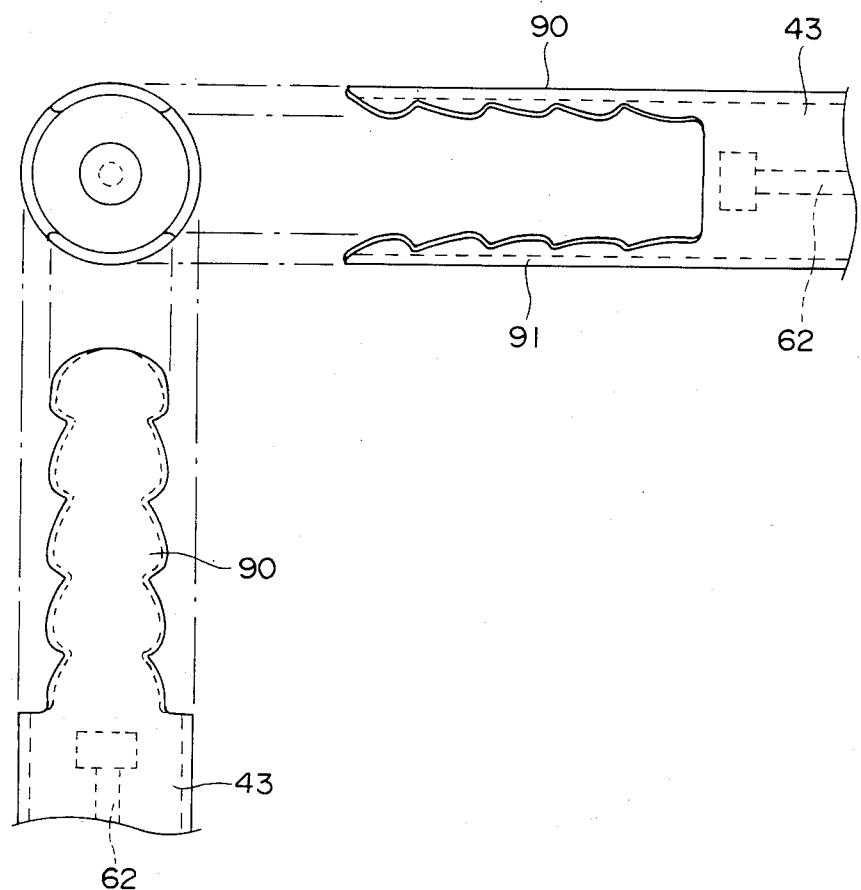
FIG. 10 is a view showing the structure of the forward end of the cylinder cleaning rod of the modification.

The structure of the forward end of the cylinder cleaning rod 43 may be as shown in FIG. 10. That is, the spring members 90, 91 each have both side edges corrugated so as to prevent a pad held therebetween from coming off in the cylinder. The forward end of the pad extruding rod 62 may be enlarged as shown by broken lines in FIG. 10 so that even when a pad is held tightly between the spring members 90, 91 the pad may be readily pushed out. The spring members 90, 91 may be separate members from the cylinder cleaning rod 43 and may be secured thereto by screws or other retainers. This facilitates the replacement of the forward end of the cylinder cleaning rod 43, which is most vulnerable to deformation and damages.

Next, the structure and the operation of the piston cleaning unit will be explained in good detail with reference to FIGS. 11, 12 and 13.

Figure 11:
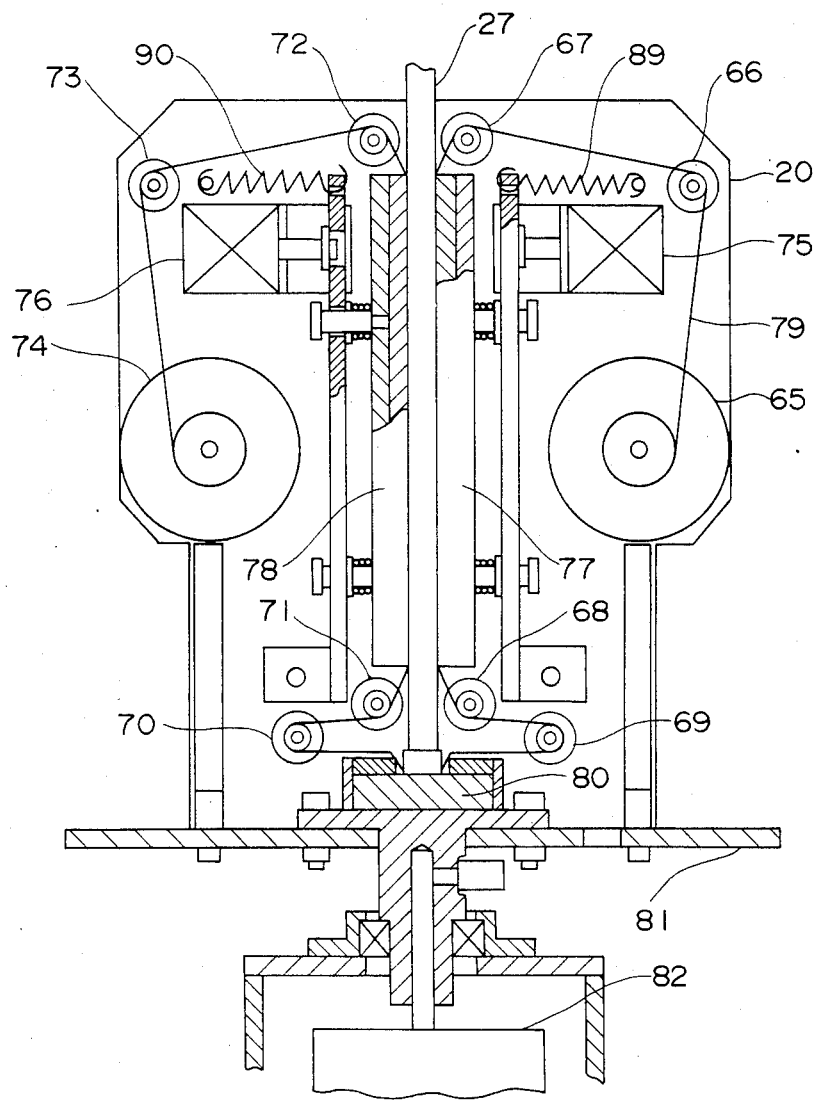
FIG. 11 is a front view of the general structure, partly in cross section, of the piston cleaning unit.

As shown in FIG. 11, a cloth tape taking-up bobbin 65, and a cloth tape supplying bobbin 74 are rotatably disposed on a piston cleaning table 20. A given length of a cloth tape 79 is wound on the cloth tape supplying bobbin 74 beforehand. The cloth tape 79 is taken up on the cloth tape taking-up bobbin 65 through rollers 66 - 73. At the center of the piston cleaning table 20 there are provided two plates 77, 78. The plates 77, 78 are urged toward each other by air cylinders 75, 76 and away from each other by springs 89, 90. The plates 77, 78 press the tape 79 extended from the bobbin 74 to he bobbin 65 against the side surface of the piston 27 to be cleaned.

The table 20 is secured to a piston cleaning mechanism 81. A disc 80 is secured to the center of the top surface of the mechanism 81. The disc 80 is for pressing the tape T9 against the forward end of the piston 27. The mechanism 81 is fixed to the rotary shaft of a motor 82. This arrangement permits the whole to rotate on the axis of the piston 27 to be cleaned.

Figure 12:
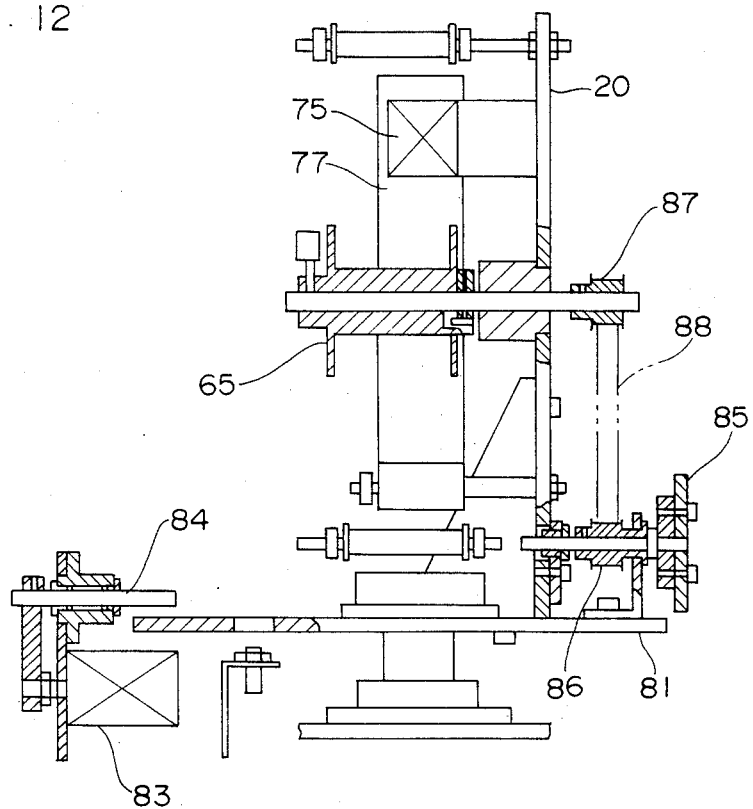
FIG. 12 is a side elevational view, partly in cross section, of the piston cleaning unit of FIG. 11.
Figure 13:
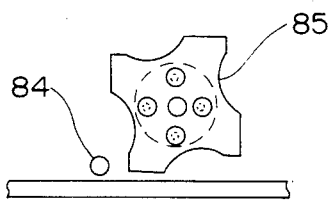
FIG. 13 is a front view of the geneva in FIG. 12.

FIGS. 12 and 13 are for explaining a driving mechanism for rotating the cloth tape taking-up bobbin 65 in FIG. 11. As shown in FIG. 12, the geneva 85 is disposed rotatably at the lower end portion of the table 20 and the rear end of the piston cleaning mechanism 81. A pulley 86 is mounted on the geneva 85. A pulley 87 is mounted on the shaft of the cloth tape taking-up bobbin 65. A timing belt 88 is extended between the pulleys 86 and 87.

An air cylinder 83 is disposed below the side end portion of the piston cleaning mechanism 81. A rod 84 is disposed above the side end portion of the mechanism 81. The air cylinder 81 moves the rod 84 inward. The forward end of the rod 84 is moved inward to abut one of four projections of the geneva 85.

The operation of the piston cleaning unit will be explained.

Before a piston cleaning is started, the cloth tape 79 which has been wound on the bobbin 74 is placed on the bobbin 65 through the rollers 66 -73. The air cylinders 75, 76 are released, and the springs 89, 90 urge the plates 77, 78 away from each other.

In this condition, a piston 27 to be cleaned is set. The piston 27 may be lowered from above or advanced toward the table from the front. When the piston 27 is set, the air cylinder 75, 78 are actuated to press the cloth tape 79 against the side surface of the piston 27. Meanwhile, the air cylinder 83 in FIG. 12 is actuated to advance the rod 84 inward.

Then the motor 82 is actuated to rotate the piston cleaning mechanism 81 and the table 20. Then the specimen residue on the surface of the piston 27 is wiped off by the tape 79. Meanwhile, every time the mechanism 81 rotates, the rod 84 abuts on the four projections of the geneva 85 one by one. This allows the geneva 85 to make a quarter rotation every time the mechanism 81 makes one rotation.

The rotation of the geneva 85 is transmitted to the cloth tape taking-up bobbin 65 through the pulley 85, the timing belt 88 and the pulley 87. This permits the bobbin 65 to make a quarter rotation every time the motor 82 makes one rotation, taking up the cloth tape 79 gradually. Accordingly, a fresh portion of the cloth tape 79 comes into contact with the piston 27 sequentially. This makes the piston cleaning effective. The vicinity of the forward end of the piston 27 can be cleaned sufficiently by moving the piston 27 vertically by an air cylinder (not shown).

When the cleaning is completed, the air cylinders 75, 76 are released to decontact the tape 79 from the piston 27, and the rod 84 is withdrawn by the air cylinder 83. Then the motor 82 is stopped, and the piston 27 is removed. The device waits for a next piston to be positioned thereon.

The piston cleaning unit is not limited to the above-described embodiment and covers modifications, reforms and variations without departing from the scope of the claims.

For example, in FIG. 11, without providing the rollers 66–68, the cloth tape 79 may be taken up from a roller 69 onto the bobbin 65. This arrangement produces the following remarkable effects. Firstly, the plate 77, the air cylinder 75, etc. can be eliminated. This makes the structure of the device simpler. Secondly, since the geneva 85 of FIG. 13 is disposed on the side of the cloth tape taking-up bobbin 65, the center of gravity does not deviate without the rollers 66–68. This improves the rotation of the table 20. Thirdly, the used portion of the cloth tape which has wiped the forward end portion of the piston 27 does not come into contact further with the side surface of the piston 27.

It produces the effect of lower noises to replace the geneva 85 with, e.g., a rubber roller and apply an anti-slip treatment to the surface of the rod 84. It is possible to mount the geneva, etc. directly on the shaft of the tape taking-up bobbin 65 without providing the pulleys 86 and 87, the timing belt 88, etc.

The tape for cleaning the piston 27 is not necessarily cloth and may be a paper tape, etc. reinforced with synthetic fibers.

Next the structure and the operation of the die cleaning unit will be explained in good detail with reference to FIGS. 14 and 15.

Figure 14:
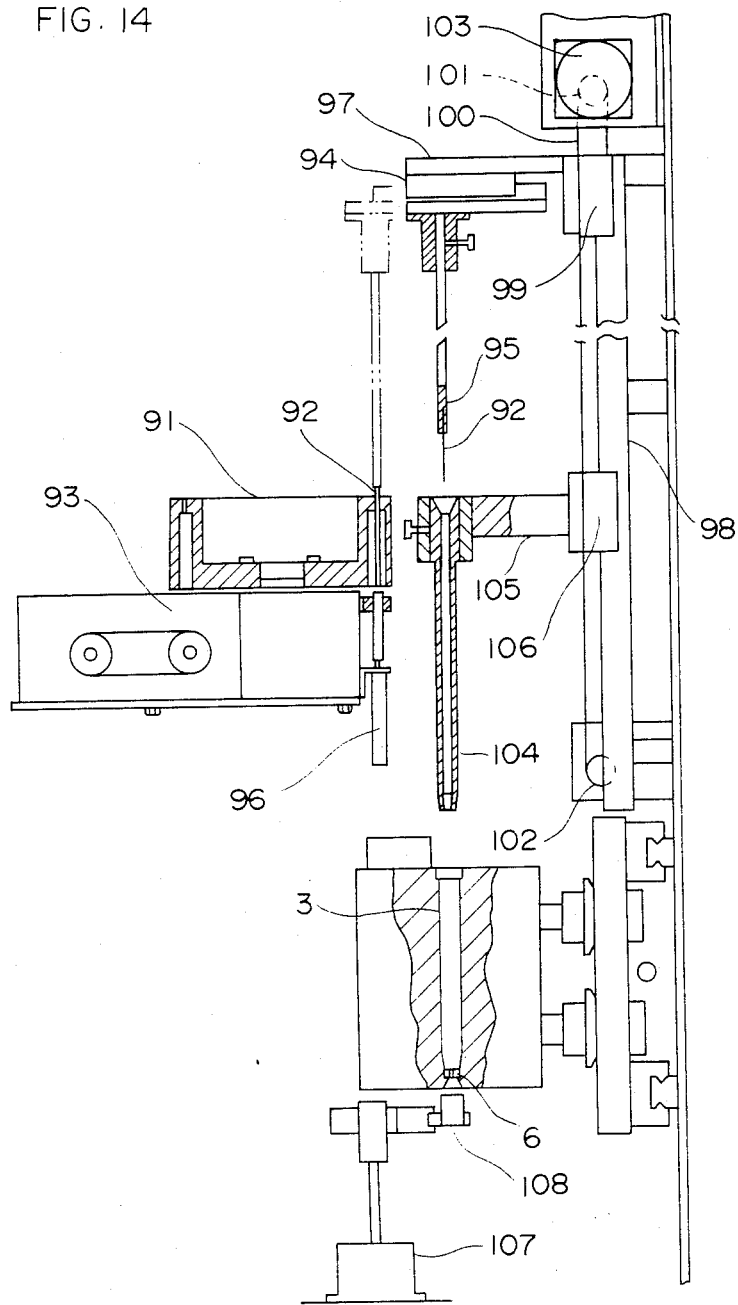
FIG. 14 is a side elevational view of the general structure, partly in cross section, of the die cleaning unit.

As shown in FIG. 14, a guide pipe 104 is arranged vertically directly above a cylinder 3 having a die 6 at the bottom thereof. Directly above the guide pipe 104 is arranged a die cleaning rod holder 95. The guide pipe 104 is secured to a guide 106 through a fixture 105. The guide 106 is movable up and down along a slide rail 98 erected. The die cleaning rod holder 95 is movable horizontally through a linear ball slide 94. The linear ball slide 94 is secured to a guide 99 through an applicator 97. This arrangement permits the die cleaning rod holder 95 to move up and down along the slide rail 98 and horizontally along the applicator 97. A reversible motor 103 moves the die cleaning rod holder 95 and the guide pipe 104 up and down. A pulley 101 is mounted on the rotary shaft of the reversible motor 103, and a timing belt 100 is wound on the pulley 101 and an idle pulley 102. The timing belt 100 is connected to the guides 99, 106.

A die cleaning rod feed table 91 is disposed near the path along which the die cleaning rod holder 95 descends. In the top surface of the die cleaning rod feed table 91 there are formed holes each of which holds a die cleaning rod upright. The die cleaning rod feed table 91 is rotated by an index drive 93, so that the die cleaning rods 92 held in the holes in the top surface of the table 91 is indexed sequentially to a feed position. Below the feed position an air cylinder for pushing up a die cleaning rod 96 is arranged, so that it pushes up one of the die cleaning rods 92 held in the holes.

Next, the operation of the first embodiment will be explained.

First, die cleaning rods 92 made of glass fiber are set in the holes of the die cleaning rod feed table 91. The index drive 93 correctly indexes the table 91, and locates one of the die cleaning rods 92 at a given position. Then the linear ball slide 94 is actuated to move the die cleaning rod holder 95 down to the position indicated by the two-dot chain line in FIG. 14 (directly above the die cleaning rod 92 set on the die cleaning rod feed table 91).

In this condition, the air cylinder for pushing up a die cleaning rod 96 pushes up one of the die cleaning rods 92, and then the die cleaning rod 92 is pushed over a given length in a bore formed in the forward end of the die cleaning rod holder 95. The die cleaning rod 92 is held vertical in the forward end of the die cleaning rod holder 95. Then the linear ball slide 94 is actuated to return the die cleaning rod holder 95 to its original position (the position indicated by the solid line in FIG. 14).

The die 6 has a small bore of about 2.095 mm in accordance with JIS. It is very difficult for the die cleaning rod 92 to enter the die 6 without guiding the rod. The reversible motor 103 is rotated to insert the guide pipe 104 into the cylinder 3. When the guide pipe 104 reaches the upper end of the die 6, a sensor acts to decontact the guide 106 from the timing belt 100, and the guide pipe 104 stops at the upper surface of the die 6.

Then the die cleaning rod holder 95 and the die cleaning rod 92 are inserted along the guide pipe 104, and the whole is inserted into the die 6 having a 2.095 mm bore. When the die cleaning rod 92 has passed through the die 6, a finger 108 is raised by a linear motor 107 to hold the die cleaning rod 92. Then the finger 108 holding the die cleaning rod 92 is lowered by the linear motor 107 to pull out the same. That is, the die cleaning rod 92 of soft glass fiber is passed through the interior of the die 6 thereby to discharge the plastics residue in the die 6 while cleaning the interior surface of the die 6. In this way, the automatic die cleaning, which has been found most difficult, is realized.

Next, a second embodiment of the die cleaning unit will be explained.

Figure 15:
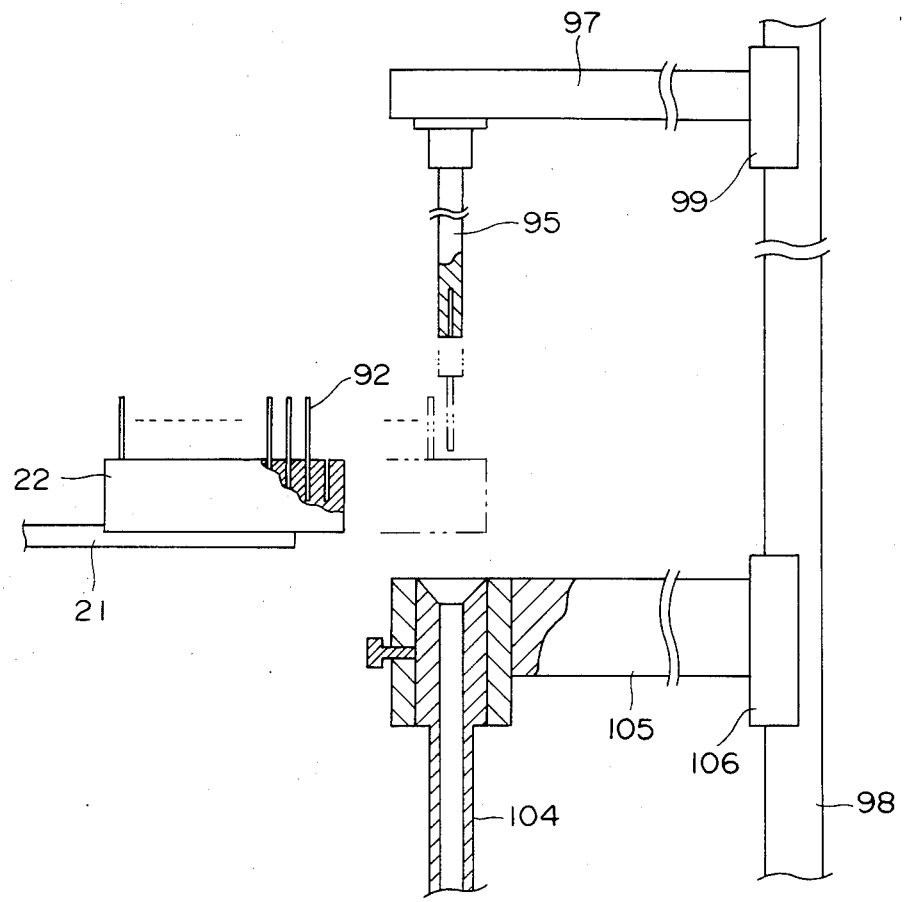
FIG. 15 is a side elevational view of a major portion of die cleaning unit according to the second embodiment.

The second embodiment as shown in FIG. 15 has the following two differences from the first embodiment as shown in FIG. 14. That is, one difference is that a plurality of die cleaning rods 92 are held on a die cleaning rod feed table 21 which is movable horizontally on a slide rail 22. The table 21 is advanced sequentially by an index drive (not shown) to position one of the die cleaning rods 92 correctly in the path along which the die cleaning rod holder 95 descends. The other difference is that there is provided no means for moving the die cleaning rod holder 95. That is, there is provided no means corresponding to the linear ball slide 94, etc. in the first embodiment.

Then the operation of the second embodiment will be explained.

In the condition indicated by the solid line in FIG. 15, the die cleaning rod feed table 22 is moved to the right along the slide rail 21 until a position indicated by the two-dot chain line in FIG. 15.

Then, the die cleaning rod holder 95 moves down along the slide rail 98, and the die cleaning rod 92 is inserted in the bore in the forward end of the die cleaning rod holder 95. The frictional force between the die cleaning rod 92 and the bore in the die cleaning rod holder 95 is made larger than that between the die cleaning rod 92 and the bores in the die cleaning rod feed table 22 so that one of the die cleaning rods 92 may be pulled out of the associated bore in the die cleaning rod feed table 22 as the die cleaning rod holder 95 goes up. This condition is shown by the two-dot chain line in FIG. 15.

Then, the die cleaning rod feed table 22 moves to the left to return to its original position. Then the die cleaning rod holder 95 and the guide pipe 104 begin to lower together along the slide rail 98. Then the die 6 at the bottom of the cylinder 3 is cleaned in the same manner as in the first embodiment shown in FIG. 14.

According to the second embodiment, the following remarkable functional advantageous effects are produced. Firstly, it is not necessary to use the linear ball slide or the like for moving the die cleaning rod holder 95 horizontally. This makes the structure of the device more compact and the cleaning of die simpler. Secondly, the die cleaning rod feed table 22 does not have to include the air cylinder for pushing up a die cleaning rod, or the like. This makes the structure of the device more compact and the cleaning of the die simpler.

The die cleaning unit is not limited to the above-described first and second embodiments and covers any modifications, reforms and variations without departing from the scope of the claims.

The means for feeding the die cleaning rod is not limited to those described in the embodiments shown in FIGS. 4 and 15. In place of the feeding means a cassette containing a plurality of die cleaning rods may be mounted on the die cleaning rod feed table. Instead, the die cleaning rods may be set on the die cleaning rod feed table by a robot, or the like, or manually. Otherwise, the die cleaning rod may be attached to the die cleaning rod holder one by one by a robot or manually.

In the embodiments, the finger pulls down a die cleaning rod out of the die, but the die cleaning rod may be pulled down from the die, e.g., by a vacuum, or the like. Instead, it makes the cleaning of the die more effective to provide separate means for rotating the finger so as to pull down the die cleaning rod out of the die while rotating the same.

Preferably the die cleaning rod is made of soft glass fiber, but the material of the rod is not limited to glass fiber. It makes the cleaning of the die easier and more effective to treat the interior surface of the die with tetrafluoride resin.

This invention is not limited to the above-described embodiment and covers reforms, modifications and variations without departing from the scope of the claims.

For example, a suitable solvent as an auxiliary material, such as liquid paraffin, may be used effectively in cleaning the cylinder and piston. The cylinder and the piston may be coated with an electrodeposited hard film, such as of chrome, and additionally surface-treated to have tetrafluoride resin chemically and physically implanted therein. Such treatment produces the effect of prohibiting a specimen from sticking to their surfaces, and the cleaning is made easier.

We claim:

1. An automatic cleaning device for use in the thermoplastics extrusion plastometer in which thermoplastics is fed into a vertically disposed cylinder to be heat melted, and the melted thermoplastics is extruded through a die formed at the bottom of the cylinder by a piston disposed at a plasticity testing position so that the plasticity of the thermoplastics is tested, said device comprising:
   a piston cleaning unit for cleaning the surface of said piston removed from said cylinder at said plasticity testing position;
   a conveying unit for moving said cylinder from said plasticity testing position sequentially to a given cylinder cleaning position and to a die cleaning position;
   a cylinder cleaning unit for cleaning the interior surface of said cylinder conveyed from said plasticity testing position to said cylinder cleaning position; and
   a die cleaning unit for cleaning the interior surface of said die conveyed from said cylinder cleaning position to said die cleaning position, without removing said die from said cylinder.

2. A device according to claim 1, wherein said piston cleaning unit comprises a table rotated on the axis of said piston by a table driving means, a tape supply bobbin mounted rotatably on said table and having a given length of tape for cleaning wound thereon, a tape taking up bobbin for taking up said tape for cleaning wound on said tape supplying bobbin mounted rotatably on said table, pressing means for pressing said tape for cleaning extended from said tape supplying bobbin to said tape taking up bobbin at least against the side surface of said piston, and bobbin driving means for rotating said tape taking up bobbin at a given speed.

3. A device according to claim 2, wherein said pressing means presses said tape for cleaning against the side surface of said piston and the forward end of said piston.

4. A device according to claim 2, wherein said pressing means comprises plates arranged parallel with said piston through said tape; air cylinders for urging said plates toward said piston; and spring members for urging said plates away from said piston.

5. A device according to claim 2, wherein said bobbin driving means comprises a geneva connected to the shaft of said tape taking-up bobbin, and a rod to abut said geneva during the rotation of said table.

6. A device according to claim 5, wherein said geneva is connected to the shaft of said tape taking-up bobbin through pulleys and a timing belt.

7. A device according to claim 1, wherein said cylinder cleaning unit comprises a cylinder cleaning rod having the forward end which can hold a pad for cleaning, and cylinder cleaning rod driving means for rotating said cylinder cleaning rod while moving the same up and down.

8. A device according to claim 1, wherein said to cylinder cleaning unit comprises:
   a cylinder cleaning rod in a cylindrical shape which has a pair of spring members for holding a pad for cleaning at the forward end thereof, and which is movable into said cylinder from above;
   cylinder cleaning rod driving means for moving up and down said cylinder cleaning rod holding a pad in said cylinder while rotating the same and withdrawing said cylinder cleaning rod out of said cylinder when cleaning is completed; and
   a pad extruding rod provided in the cylinder cleaning rod in a cylindrical shape for pushing downward the pad held by said spring members when the cylinder cleaning rod is withdrawn out of said cylinder.

9. A device according to claim 8, wherein said spring members are provided by bisecting the forward end of said cylinder cleaning rod.

10. A device according to claim 8, wherein said spring members include corrugated inside surfaces.

11. A device according to claim 8, wherein said spring members include corrugated side edges.

12. A device according to claim 8, wherein said cylinder cleaning rod is lowered by its own weight.

13. A device according to claim 8, wherein said pad extruding rod is advanced by an air cylinder.

14. A device according to claim 1, wherein said cylinder cleaning unit comprises:
   a pad stocker for storing a plurality of pads for cleaning;
   a feed mechanism for feeding said pads one by one from said pad stocker;
   a cylinder cleaning rod in a cylindrical shape which has a pair of spring members for holding a pad for cleaning at the forward end thereof, and which is movable into said cylinder from above;
   a pad holder for holding one of said pads fed from said pad stocker at its original position, and movable so that the held pad may be positioned in a path along which said cylinder cleaning rod is lowered toward said cylinder, and returned to its original position after said pad has been held by the spring members of said cylinder cleaning rod;
   cylinder cleaning rod driving means for moving up and down said cylinder cleaning rod holding a pad in said cylinder while rotating the same and withdrawing the cylinder cleaning rod out of said cylinder when a cleaning is completed; and
   a pad extruding rod provided in the cylinder cleaning rod in a cylindrical shape for pushing downward the pad held by said spring members when the cylinder cleaning rod is withdrawn out of said cylinder.

15. A device according to claim 14, wherein said pad stocker stores said pads in a stack.

16. A device according to claim 14, wherein said feed mechanism includes a mechanism for pushing out the undermost one of the pads in the stack to said original position of said pad holder by pushing means.

17. A device according to claim 14, wherein said spring members are provided by bisecting the forward end of said cylinder cleaning rod.

18. A device according to claim 14, wherein said spring members include corrugated inside surfaces.

19. A device according to claim 14, wherein said spring members include corrugated side edges.

20. A device according to claim 14, wherein said cylinder cleaning rod is lowered by its own weight.

21. A device according to claim 14, wherein said pad extruding rod is advanced by an air cylinder.

22. A device according to claim I, wherein said die cleaning unit comprises a die cleaning rod holder for inserting said die cleaning rod into said die through said cylinder, die cleaning rod discharging means for pulling out said die cleaning rod projected through said die downward of said cylinder.

23. A device according to claim 1, wherein said die cleaning unit comprises:
- a die cleaning rod holder vertically movably provided directly above said cylinder and having a bore for a die cleaning rod to be vertically inserted into the lower end thereof;
- a guide pipe vertically movably provided directly below said die cleaning rod holder for guiding said die cleaning rod holder into said cylinder;
- driving means for moving up and down said die cleaning rod holder and said guide pipe; and
- means for discharging said die cleaning rod passed through said die and projecting downward from said die, provided below said die at the bottom of said cylinder.

24. A device according to claim 23, wherein said driving means comprises a slide rail erected parallel with the axis of said cylinder and a motor for moving up and down said die cleaning rod holder and said guide pipe.

25. A device according to claim 23, wherein said means for discharging said die cleaning rod comprises a finger which is driven to hold said die cleaning rod projected downward from said die and pull down said die cleaning rod out of said die.

26. A device according to claim 1, wherein said die cleaning unit comprises:
- a die cleaning rod holder vertically movably provided directly above said cylinder and having a bore for a die cleaning rod to be vertically inserted into the lower end thereof;
- a guide pipe provided vertically movably directly below said die cleaning rod holder for guiding said die cleaning rod holder into said cylinder;
- means for feeding a die cleaning rod which holds a plurality of said die cleaning rods and feeds one of said die cleaning rods into said bore of said die cleaning rod holder whenever said die is cleaned;
- driving means for moving up and down said die cleaning rod holder and said guide pipe; and means for discharging said die cleaning rod which has passed through said die and is projected downward from said die, provided below said die at the bottom of said cylinder.

27. A device according to claim 26, wherein said die cleaning rod feed means comprises a die cleaning rod feed table having a plurality of bores formed in the top surface thereof for holding said plurality of said die cleaning rods vertical; means for driving said die cleaning rod feed table so that said plurality of bores may be located one by one at a given die cleaning rod feed position; and means for driving said die cleaning rod holder so that the forward end of said die cleaning rod holder may be located at said die cleaning rod feed position.

28. A device according to claim 26, wherein said die cleaning rod feed means comprises a die cleaning rod feed table having a plurality of bores formed in the top surface thereof for holding said plurality of said die cleaning rods vertical; and means for driving said die cleaning rod feed table horizontally so that said plurality of said bores may be located sequentially in the path along which said die cleaning rod holder lowers.

29. A device according to claim 26, wherein said driving means comprises a slide rail erected parallel with the axis of said cylinder and a motor for moving up and down said die cleaning rod holder and said guide pipe.

30. A device according to claim 26, wherein said means for discharging said die cleaning rod comprises a finger which is driven to hold said die cleaning rod projected downward from said die and pull down said die cleaning rod out of said die.

31. A device according to claim 1, wherein the interior surface of said cylinder and the exterior surface of said piston are coated with an electrodeposited hard film of chrome or others and additionally are surface-treated to have tetrafluoride resin implanted therein.

32. A device according to claim 1, wherein the interior surface of said die is coated with fluoride film.

33. A device according to claim 8, wherein said cylinder cleaning rod is lowered by a predetermined load.

34. A device according to claim 14, wherein said cylinder cleaning rod is lowered by a predetermined load.

* * * * *